United States Patent [19]

Misslitz et al.

[11] Patent Number: 5,618,775
[45] Date of Patent: Apr. 8, 1997

[54] MIXTURES OF OPTICALLY ACTIVE CYCLOHEXENONE OXIME ETHERS, THEIR PREPARATION, INTERMEDIATES FOR THIS PURPOSE AND THEIR USE AS HERBICIDES

[75] Inventors: Ulf Misslitz, Neustadt; Norbert Meyer, Ladenburg; Juergen Kast, Boehl-Iggelheim; Wolfgang Ladner, Fussgoenheim; Helmut Walter, Obrigheim; Karl-Otto Westphalen, Speyer; Uwe Kardorff, Mannheim; Matthias Gerber, Mutterstadt, all of Germany

[73] Assignee: BASF Aktiengesellschaft, Ludwigshafen, Germany

[21] Appl. No.: 290,726

[22] PCT Filed: Jan. 30, 1993

[86] PCT No.: PCT/EP93/00210

§ 371 Date: Aug. 11, 1994

§ 102(e) Date: Aug. 11, 1994

[87] PCT Pub. No.: WO93/16061

PCT Pub. Date: Aug. 19, 1993

[30] Foreign Application Priority Data

Feb. 13, 1992 [DE]  Germany .......................... 42 04 204.6

[51] Int. Cl.⁶ .......................... A01N 43/60; A01N 43/16; C07D 241/44; C07D 309/06
[52] U.S. Cl. .......................... 504/235; 504/250; 504/251; 504/252; 504/253; 504/256; 504/267; 504/270; 504/271; 504/280; 504/288; 504/289; 504/290; 504/291; 504/292; 504/293; 504/294; 504/295; 504/315; 504/344; 544/354; 546/261; 546/280.1; 546/280.4; 546/281.7; 546/282.1; 546/283.4; 546/283.7; 546/272.1; 546/275.4; 546/300; 548/170; 548/221; 548/243; 548/247; 548/366.1; 548/366.4; 548/373.1; 549/9; 549/13; 549/28; 549/426; 549/416; 549/417; 549/346; 560/16; 560/35; 564/256; 564/348
[58] Field of Search .......................... 549/13, 426, 9, 549/416, 346, 417, 28; 564/256; 548/247, 373.1, 221, 170, 243, 366.1, 366.4; 546/268, 300, 279, 275, 261, 280.1, 280.4, 281.7, 282.1, 272.1, 283.4, 283.7; 544/354; 560/16, 35; 504/288–295, 315, 344, 271, 280, 251–253, 256, 270, 267, 235, 282, 250

[56] References Cited

U.S. PATENT DOCUMENTS

| 4,440,566 | 4/1984 | Luo ................................ 504/313 |
| 4,624,696 | 11/1986 | Keil et al. ........................ 504/246 |
| 5,190,573 | 3/1993 | Misslitz et al. .................. 504/292 |
| 5,496,792 | 3/1996 | Misslitz et al. .................. 504/100 |
| 5,514,642 | 5/1996 | Misslitz et al. .................. 504/244 |

FOREIGN PATENT DOCUMENTS 080301  6/1983  European Pat. Off. .
089115  9/1983  European Pat. Off. .
205821  12/1986  European Pat. Off. .
238021  9/1987  European Pat. Off. .
368227  5/1990  European Pat. Off. .
125094  4/1991  European Pat. Off. .
230665  9/1988  Japan ................................ 546/300
9310081  5/1993  WIPO ................................ 564/256

OTHER PUBLICATIONS

Sumitomo Chemical Co. *Chem. Abst.*, vol. 102, No. 19, May 13, 1985, Abstract No. 166459f, p. 591 (English abstract of JP-A 60/006645).

Go et al *Chem. Abst.*, vol. 111, No. 17, Oct. 23, 1989, Abstract No. 153345b, p. 674 (English abstract of JP-A 63/230665).

*Primary Examiner*—Emily Bernhardt
*Attorney, Agent, or Firm*—Keil & Weinkauf

[57] ABSTRACT

Mixtures of optically active cyclohexenone oxime ethers having R- and S-configuration in the oxime ether moiety of the formula I ($R^1 = C_1 - C_6$-alkyl;

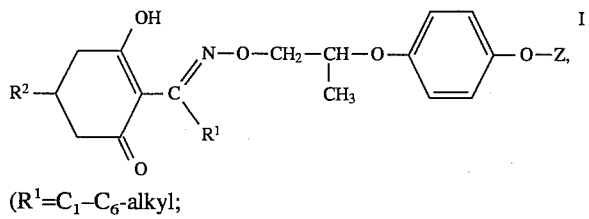

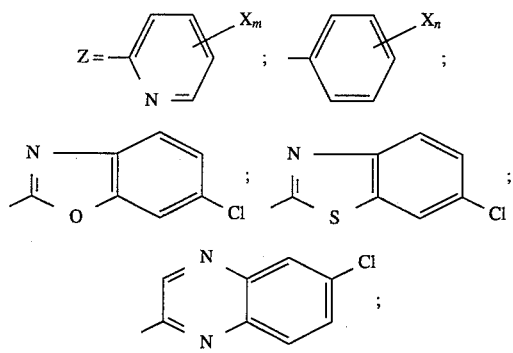

$X = C_1 - C_4$-alkyl, $C_1 - C_4$-haloalkyl;
m=0–3 or 1–4 where all X's are halogen;
n=0–3 or 1–5 where all X's are halogen;
$R^2 = C_1 - C_4$-alkoxy-$C_1 - C_6$-alkyl, $C_1 - C_4$-alkylthio-$C_1 - C_6$-alkyl, substituted or unsubstituted $C_3 - C_7$-cycloalkyl, substituted or unsubstituted $C_5 - C_7$-cycloalkenyl, substituted or unsubstituted 5-membered saturated heterocyclic structure, substituted or unsubstituted 6- or 7-membered heterocyclic structure, substituted or unsubstituted 5-membered heteroaromatic structure, substituted or unsubstituted phenyl or pyridyl)
and their agriculturally useful salts and esters with $C_1 - C_{10}$-carboxylic acids and inorganic acids.

6 Claims, No Drawings

_5,618,775_

MIXTURES OF OPTICALLY ACTIVE CYCLOHEXENONE OXIME ETHERS, THEIR PREPARATION, INTERMEDIATES FOR THIS PURPOSE AND THEIR USE AS HERBICIDES

This application is a 371 of PCT/EP93/00210, filed Jan. 30, 1993.

The present invention relates to novel mixtures of optically active cyclohexenone oxime ethers having the R- and S-configuration in the oxime ether moiety and of the general formula I $$\text{R}^2 \underset{\underset{\text{O}}{\parallel}}{\overset{\overset{\text{OH}}{\mid}}{\text{C}}} \overset{\text{N}-\text{O}-\text{CH}_2-\text{CH}-\text{O}-\underset{\text{CH}_3}{\mid}-\text{O}-\text{Z}}{\underset{\text{R}^1}{\parallel}} \qquad \text{I}$$

where $R^1$ is $C_1$–$C_6$-alkyl;

Z is one of the following groups:

[pyridyl with $X_m$]; [phenyl with $X_n$];

[benzoxazolyl-Cl]; [benzothiazolyl-Cl];

[quinoxalinyl-Cl];

X is halogen or $C_1$–$C_4$-haloalkyl;

m is from 0 to 3, or from 1 to 4 where all X are halogen;

n is from 0 to 3, or from 1 to 5 where all X are halogen;

$R^2$ is $C_1$–$C_4$-alkoxy-$C_1$–$C_6$-alkyl or $C_1$–$C_4$-alkylthio-$C_1$–$C_6$-alkyl;

$C_3$–$C_7$-cycloalkyl or $C_5$–$C_7$-cycloalkenyl, where these groups may, if desired, carry from one to three substituents selected from the group consisting of $C_1$–$C_4$-alkyl, $C_1$–$C_4$-alkoxy, $C_1$–$C_4$-alkylthio, $C_1$–$C_4$-haloalkyl, hydroxyl and halogen;

a 5-membered saturated heterocyclic structure which contains one or two oxygen and/or sulfur atoms as hetero atoms and may, if desired, furthermore carry from one to three substituents selected from the group consisting of $C_1$–$C_4$-alkyl, $C_1$–$C_4$-alkoxy, $C_1$–$C_4$-alkylthio and $C_1$–$C_4$-haloalkyl;

a 6-membered or 7-membered saturated or mono- or di-unsaturated heterocyclic structure which contains one or two oxygen or sulfur atoms or one oxygen and one sulfur atom as hetero atoms and may, if desired, furthermore carry from one to three substituents selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl;

a 5-membered heteroaromatic structure containing from one to three hetero atoms selected from the group consisting of one or two nitrogen atoms and one oxygen or sulfur atom, where the heteroaromatic structure may, if desired, furthermore carry from one to three substituents selected from the group consisting of halogen, cyano, $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy and $C_1$–$C_4$-alkoxy-$C_1$–$C_4$-alkyl; phenyl or pyridyl, where these aromatic structures may, if desired, furthermore carry from one to three substituents selected from the group consisting of halogen, nitro, cyano, $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, $C_3$–$C_6$-alkynyloxy and an amino group —$NR^aR^b$, where $R^a$ is hydrogen, $C_1$–$C_4$-alkyl, $C_3$–$C_6$-alkenyl or $C_3$–$C_6$-alkynyl, $R^b$ is hydrogen, $C_1$–$C_4$-alkyl, $C_3$–$C_6$-alkenyl, $C_3$–$C_6$-alkynyl, $C_1$–$C_6$-acyl or benzoyl which, if desired, in turn may furthermore carry from one to three radicals selected from the group consisting of nitro, cyano, halogen, $C_1$–$C_4$-alkyl, $C_1$–$C_4$-alkoxy, $C_1$–$C_4$-alkylthio and $C_1$–$C_4$-haloalkyl, and the agriculturally useful salts and esters of the compounds I with $C_1$–$C_{10}$-carboxylic acids and inorganic acids.

The present invention furthermore relates to a process for the preparation of these compounds, their use as herbicides, and herbicides which contain these mixtures.

The present invention also relates to novel mixtures of optically active hydroxylamines having the R- and S-configuration of the formula III $$\text{H}_2\text{N}-\text{O}-\text{CH}_2-\underset{\underset{\text{CH}_3}{\mid}}{\text{CH}}-\text{O}-\underset{}{\boxed{\phantom{xx}}}-\text{O}-\text{Z} \qquad \text{III}$$

where

Z is one of the following groups:

[pyridyl with $X_m$]; [phenyl with $X_n$];

[benzoxazolyl-Cl]; [benzothiazolyl-Cl];

[quinoxalinyl-Cl];

where

X is halogen or $C_1$–$C_4$-haloalkyl, m is from 0 to 3, or from 1 to 4 where all X are halogen, and n is from 0 to 3, or from 1 to 5 where all X are halogen.

The literature discloses herbicidal cyclohexanediones of the formula I'

$$\text{R}^e \underset{\underset{\text{O}}{\parallel}}{\overset{\overset{\text{OH}}{\mid}}{\text{C}}} \overset{\text{N}-\text{O}-\text{R}^d}{\underset{\text{R}^c}{\parallel}} \qquad \text{I}'$$

where $R^c$, $R^d$ and $R^e$ have, inter alia, the following meanings:

U.S. Pat. No. 4,440,566 ($R^c$ is ethyl or propyl, $R^d$ is benzyl and $R^e$ is 2-ethylthiopropyl);

EP-A 238 021 and EP-A 125 094 ($R^c$ is ethyl or propyl, $R^d$ is benzyl or but-2-enyl and $R^e$ is a substituted 5-membered hetaryl radical);

EP-A 80 301 ($R^c$ is ethyl or propyl, $R^d$ is benzyl or but-2-enyl and $R^e$ is substituted phenyl);

DE-A 38 38 309 ($R^c$ is ethyl or propyl, $R^d$ is a substituted 4-phenylbutylene or 4-phenylbutenylene radical and $R^e$ is a substituted 5-membered to 7-membered heterocyclic structure);

EP-A 456 112 ($R^c$ is ethyl or propyl, $R^d$ is a substituted 3-phenoxypropylene or 2-phenoxyethylene radical and $R^e$ is a substituted 5-membered to 7-membered heterocyclic structure).

However, the herbicidal properties of these compounds, particularly with regard to their selectivity toward grass weeds in gramineous crops, may be satisfactory only to a limited extent.

Hence, it was an object of the present invention to provide novel mixtures of cyclohexenone oxime ethers having improved selectivity towards grass weeds in gramineous crops, such as rice and corn.

We have found that this object is achieved by the mixtures of optically active cyclohexenone oxime ethers I, defined at the outset. We have also found herbicides which contain these mixtures.

The mixtures of optically active cyclohexenone oxime ethers I are obtainable by various methods, preferably in a conventional manner from known cyclohexenones of the formula II (DE-A 38 38 309, EP-A 243 313 and EP-A 456 112) and the corresponding mixtures of optically active hydroxylamines having the R- and S-configuration of the formula III (cf. EP-A 169 521):

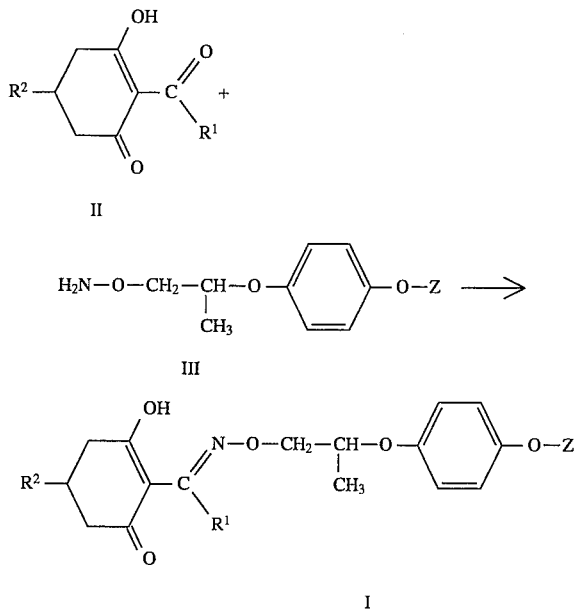

A suitable salt of the hydroxylamines III is preferably used, in particular the hydrochloride thereof, and the reaction is carried out in the heterogeneous phase in an inert solvent, for example in dimethyl sulfoxide, an alcohol, such as methanol, ethanol and isopropanol, an aromatic hydrocarbon, such as benzene and toluene, a chlorohydrocarbon, such as chloroform and 1,2-dichloroethane, an aliphatic hydrocarbon, such as hexane and cyclohexane, an ester, such as ethyl acetate, or an ether, such as diethyl ether, dioxane and tetrahydrofuran.

The reaction is carried out in the presence of a base, from about 0.5 to 2 mol equivalents, based on the ammonium compound, of a base usually being sufficient, Examples of suitable bases are carbonates, hydrocarbonates, acetates, alcoholates or oxides of alkali or alkaline earth metals, in particular sodium hydroxide, potassium hydroxide, magnesium oxide or calcium oxide. Organic bases, such as pyridine and tertiary amines, eg. triethylamine, are also suitable.

The reaction is preferably carried out in methanol, using sodium bicarbonate as the base.

In a variant of the process, the reaction is carried out in the absence of a base, using the free hydroxylamine bases III, for example in the form of an aqueous solution; depending on the solvent used for the compound II, a one- or two-phase reaction mixture is obtained.

Examples of suitable solvents for this variant are alcohols, such as methanol, ethanol, isopropanol and cyclohexanol, aliphatic and aromatic hydrocarbons and chlorohydrocarbons, such as hexane, cyclohexane, methylene chloride, toluene and 1,2-dichloroethane, esters, such as ethyl acetate, nitriles, such as acetonitrile, and cyclic ethers, such as dioxane and tetrahydrofuran.

The cyclohexenone II and the mixture of optically active hydroxylamines III or the salts thereof are expediently used in a roughly stoichiometric ratio, with in some cases an excess of up to about 10 mol % of one or the other component may also be advantageous.

The reaction temperatures in general are from 0° C. to the boiling point of the reaction mixture, preferably from 20° to 80° C.

The reaction is complete after a few hours. The product can be isolated in a conventional manner, for example by evaporating down the mixture, partitioning the residue between methylene chloride and water and distilling off the solvent under reduced pressure.

There is no need to ensure particular conditions with regard to the pressure; in general, the reaction is therefore carried out at atmospheric pressure or under the autogenous pressure of the particular diluent.

Owing to their acidic character, the optically active cyclohexenone oxime ethers I can form salts of alkali or alkaline earth metal compounds and enol esters.

Alkali metal salts of the compounds I can be obtained by treating the 3-hydroxycyclohexenone compounds with sodium hydroxide, potassium hydroxide or a sodium or potassium alcoholate in aqueous solution or in an organic solvent, such as methanol, ethanol, acetone and toluene.

Other metal salts, such as manganese, copper, zinc, iron, calcium, magnesium and barium salts, can be prepared from the sodium salts in a conventional manner, as can ammonium and phosphonium salts by means of ammonia or phosphonium, sulfonium or sulfoxonium hydroxides.

The esters of the compounds I are likewise obtainable in a conventional manner (cf. for example Organikum, VEB Deutscher Verlag der Wissenschaften, 17th Edition, Berlin 1988, pages 405–408).

The novel mixtures of optically active hydroxylamines III can be prepared via a number of known process steps, starting from known intermediates:

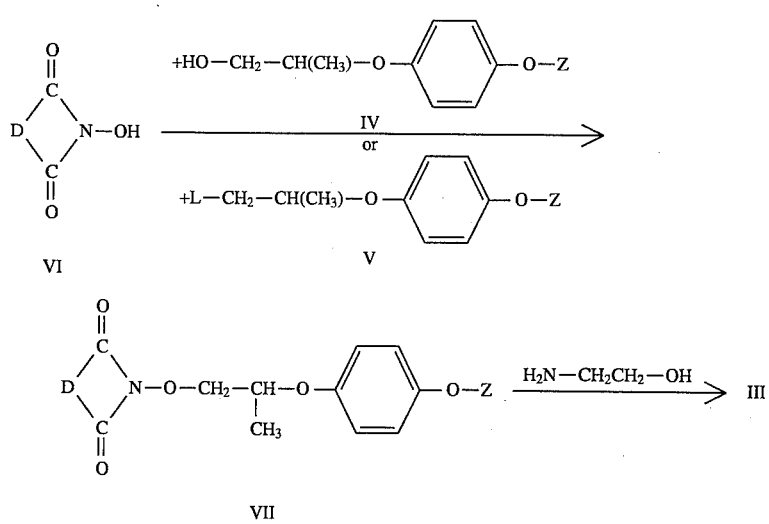

L=a leaving group, eg. halogen, such as chlorine, bromine or iodine, or CH$_3$SO$_2$—O—.

The optically active alkylating agent V (Z. Naturforsch. 37 B (1982), 912; DE-A 26 11 695) or, if desired, the optically active carbinol IV (Z. Naturforsch. 37 B (1982), 912; DE-A 26 11 695; U.S. Pat. No. 4,491,468; EP-A 003 877; DE-A 25 43 179; DE-A 26 49 706; DE-A 24 15 867) is preferably coupled by the Mitsunobu method (Synthesis 1, 1981; J. Med. Chem. 33 (1990), 187) with a cyclic hydroximide VI, and the resulting protected hydroxylamine derivative VII is cleaved, for example with 2-aminoethanol, to give the free hydroxylamine III.

In the cyclic hydroximides VI, D is, for example, C$_2$ or C$_3$-alkylene, C$_2$-alkenylene or a 5-membered or 6-membered ring which may have a nitrogen atom and may be saturated, partially unsaturated or aromatic, for example phenylene, pyridylene, cyclopentylene, cyclohexylene or cyclohexenylene.

Examples of suitable substances are the following:

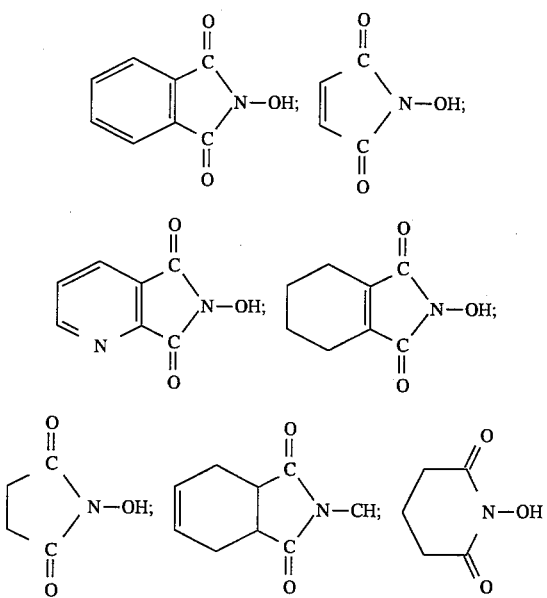

The reaction of the optically active alkylating agent V with the hydroximide VI is advantageously carried out in the presence of a base. All bases which are capable of deprotonating the hydroximides VI without attacking the imide system are in principle suitable. These are in particular the nonnucleophilic bases.

Examples are mineral bases, such as alkali metal and alkaline earth metal carbonates, and alkali metal and alkaline earth metal bicarbonates, and organic bases, such as aliphatic, cycloaliphatic and aromatic tertiary amines. However, mixtures of these bases may also be used.

Examples of individual compounds are the following bases: sodium carbonate, potassium carbonate, magnesium carbonate, calcium carbonate, barium carbonate, the bicarbonates of these metals, trimethylamine, triethylamine, tributylamine, ethyldiisopropylamine, N,N-dimethylaniline, 4-(N,N-dimethylamino)-pyridine, diazabicyclooctane, diazabicycloundecane, N-methylpiperidine, 1,4-dimethylpiperazine, pyridine, quinoline, bipyridine and phenanthroline. The economical bases sodium carbonate and potassium carbonate are preferred.

The base is added in general in an equivalent amount to an excess of 5 equivalents, based on the hydroximide. A greater excess is possible but generally has no additional advantages. It is also possible to use a small amount of base. However, from 1 to 3, in particular from 1 to 2, equivalents, based on the hydroximide VI, of a base are preferably used.

The use of nucleophilic bases, for example alkali metal and alkaline earth metal hydroxides, in particular sodium hydroxide and potassium hydroxide, is also possible. In this case, it is also advantageous to use the base in equivalent amounts, based on the hydroximide VI, in order to avoid a nucleophilic attack by the hydroxyl ions on the carbonyl function of the imide group.

The optically active alkylating agents V are expediently reacted with the hydroximides VI in a solvent which is inert under the reaction conditions. Examples of advantageous solvents are polar, aprotic solvents, such as dimethylformamide, N-methylpyrrolidone, dimethyl sulfoxide, sulfolane and cyclic ureas. The amount of solvent is in general not critical.

The reaction of the optically active alkylating agent V with the hydroximide VI can also be carried out using phase transfer catalysis. In this case, solvents which form two phases with water are used, preferably chlorohydrocarbons. Suitable phase transfer catalysts are the quaternary ammonium and phosphonium salts, polyethylene glycols, polyethylene glycol ethers and crown ethers usually used for such purposes, as described, for example, by Dehmlow et al., Phase Transfer Catalysis, pages 37–45 and 86–93, Verlag Chemie, Weinheim 1980.

The phase transfer catalysts are advantageously used in amounts of from 1 to 10, preferably from 3 to 5%, by volume, based on the volume of the reaction mixture.

The reaction of the optically active alkylating agent V with the hydroximide VI is carried out in general at from 0° to 140° C., preferably from 2° to 100° C., in particular from 40° to 80° C. In an advantageous procedure, the hydroximide VI is initially taken together with the base in the solvent, and the alkylating agent V is metered into this solution. It may prove advantageous if the hydroximide is added at a lower temperature, for example at from 0° to 50° C., and the reaction mixture is heated to the actual reaction temperature only after this addition.

After the end of the reaction, water is expediently added to the cooled reaction mixture, the resulting hydroxylamine derivatives VII separating out as a crystalline solid or as an oil. The hydroxylamine derivatives obtained in this manner can, if desired, be further purified by recrystallization or by extraction.

The hydroxylamine derivative VII may be temporarily stored or immediately converted into the optically active hydroxylamines III having a free amino group.

This conversion can be carried out by a conventional process, as described, for example, in DE-A 36 15 973 and the publications cited therein. The process according to DE-A 36 15 973, in which the optically active hydroxylamines III were liberated by means of ethanolamine, are preferably used. Liberation of the hydroxylamines III with the aid of other bases, such as aqueous mineral bases, with a mines, hydrazines or hydroxylamines or by means of aqueous acids is also possible.

The optically active hydroxylamines III can be isolated from the reaction mixtures obtained in these processes by means of conventional methods of working up, for example by extraction or by crystallization. To increase the tendency of these hydroxylamines III to crystallize, it may often be advantageous to convert them into their salts with mineral acids or organic acids. For this purpose, in general dilute solutions of these acids are reacted with the hydroxylamine derivatives, expediently in roughly equivalent amounts. The hydroxyl ammonium salts obtained can, as the optically active hydroxylamines III (with free amino group), be directly further processed to give the optically active cyclohexenone oxime ethers of the formula I or, if desired, can also be stored.

The optical purity of the intermediates III and of the cyclohexenone oxime ether I depends on the optical purity of the carbinols IV or alkylating agents V used. The carbinols IV and the alkylating agents V are preferably used as mixtures, containing at least 50 mol % of R isomers, so that, in the preparation of the optically active hydroxylamines III and of the optically active cyclohexenone oxime ethers I, isomer mixtures containing at least 50, preferably from 90 to 100, mol % of isomers having the R-configuration at the methyl-substituted carbon atom (in the oxime ether moiety) are obtained in each case.

Depending on the substituents, the optically active cyclohexenone oxime ethers I may be obtained in the preparation also in the form of the E/Z isomer mixtures, the isomers differing due to the position of the oxime ether moiety relative to $R^1$. The E and Z isomers can, if desired, be separated by a conventional method, for example by chromatography or by crystallization.

The optically active cyclohexenone oxime ethers I may be written in a plurality of tautomeric forms, and the present invention relates to all of these forms.

The collective terms used in the definition of the substituents halogen $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy, $C_3$–$C_6$-alkenyl, $C_3$–$C_6$-alkenyloxy, $C_3$–$C_6$-alkynyl, $C_3$–$C_6$-alkynyloxy, $C_1$–$C_6$-acyl are shorthand for an individual listing of the specific group members. All the alkyl, alkoxy, alkylthio, haloalkyl, alkenyl, alkenyloxy, alkynyl and alkynyloxy moieties may be straight-chain or branched. The haloalkyl moieties may carry identical or different halogen atoms. Specific examples are as follows:

halogen: fluorine, chlorine, bromine and iodine;

$C_1$–$C_4$-alkyl: methyl, ethyl, n-propyl, 1-methylethyl, n-butyl, 1-methylpropyl, 2-methylpropyl and 1,1-dimethylethyl;

$C_1$–$C_4$-alkoxy: methoxy, ethoxy, n-propoxy, 1-methylethoxy, n-butoxy, 1-methylpropoxy, 2-methylpropoxy and 1,1-dimethylethoxy;

$C_1$–$C_4$-alkylthio: methylthio, ethylthio, n-propylthio, 1-methylethylthio, n-butylthio, 1-methylpropylthio, 2-methylpropylthio and 1,1-dimethylethylthio;

$C_1$–$C_4$-haloalkyl: fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trifluoroethyl, 2-chloro-2,2-difluoroethyl, 2,2-dichloro-2-fluoroethyl, 2,2,2-trichloroethyl and pentafluoroethyl;

$C_2$–$C_6$-alkenyl: ethenyl and $C_3$–$C_6$-alkenyl, such as 1-propenyl, 2-propenyl, 1-methylethenyl, 1-butenyl, 2-butenyl, 3-butenyl, 1-methyl-1-propenyl, 1-methyl-2-propenyl, 2-methyl-1-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl;

$C_2$–$C_6$-alkenyloxy: ethenyloxy and $C_3$–$C_6$-alkenyloxy, such as 2-propenyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1,1-dimethyl-2-propenyloxy, 1,2-dimethyl-2-propenyloxy, 1-ethyl-2-propenyloxy, 2-hexenyloxy, 3-hexenyloxy, 4-hexenyloxy, 5-hexenyloxy, 1-methyl-2- pentenyloxy, 2-methyl-2-hexenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, 4-methyl-4-pentenyloxy, 1,1-dimethyl-2-butenyloxy, 1,2-dimethylpentenyloxy, 2-butenyloxy, 1,2-dimethyl-3-butenyloxy, 1,3-dimethyl-2-butenyloxy, 1,3-dimethyl-3-butenyloxy, 2,2-dimethyl-3-butenyloxy, 2,3-dimethyl-2-butenyloxy, 2,3-dimethyl- 3-butenyloxy, 1-ethyl-2-butenyloxy, 1-ethyl-3-butenyloxy, 2-ethyl-2-butenyloxy, 2-ethyl-3-butenyloxy, 1,1,2-trimethyl-2-propenyloxy, 1-ethyl-1-methyl-2-propenyloxy and 1-ethyl-2-methyl-2-propenyloxy.

In view of their herbicidal activity, preferred mixtures of optically active cyclohexenones of the formula I are those in which $R^1$ is $C_1$–$C_6$-alkyl, such as methyl, ethyl, n-propyl, n-butyl, n-pentyl and n-hexyl, preferably ethyl and propyl;

Z is one of the following groups:

particularly preferably

X is halogen, such as fluorine, chlorine, bromine and iodine, perferably fluorine, chlorine or bromine, or $C_1$–$C_4$-haloalkyl, preferably difluoromethyl, trifluoromethyl, 2,2,2-trifluoroethyl or pentafluoroethyl, particularly preferably halogen or trifluoromethyl;

m is from 0 to 3, or from 1 to 4 where all X are halogen, preferably from 0 to 3;

n is from 0 to 3, or from 1 to 5 where all X are halogen, preferably from 0 to 3;

$R^2$ is $C_1$–$C_6$-alkyl, such as methyl, ethyl, n-propyl, 1-methylethyl, n-butyl, 1-methylpropyl, 2-methylpropyl and 1,1-dimethylethyl, n-pentyl, 1-methylbutyl, 2-methylbutyl, 3-methylbutyl, 1,1-dimethylpropyl, 1,2-dimethylpropyl, 2,2-dimethylpropyl, 1-ethylpropyl, n-hexyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl, where the alkyl group is substituted by $C_1$–$C_4$-alkoxy, preferably methoxy, ethoxy, 1-methylethoxy or 1,1-dimethylethoxy, or by $C_1$–$C_4$-alkylthio, preferably methylthio or ethylthio, preferably in the 1-, 2- or 3-position, very particularly preferably 2-ethylthiopropyl;

$C_3$–$C_7$-cycloalkyl or $C_5$–$C_7$-cycloalkenyl, such as cyclopropyl, cyclobutyl, cyclopentyl, cyclohexyl, cycloheptyl, cyclopentenyl, cyclohexenyl or cycloheptenyl, where these groups may be unsubstituted or may carry from one to three of the following substituents: $C_1$–$C_4$-alkyl, preferably methyl, $C_1$–$C_4$-alkoxy, $C_1$–$C_4$-alkylthio and $C_1$–$C_4$-haloalkyl, very particularly preferably 1-methylthio-1-cyclopropyl;

a 5-membered saturated heterocyclic structure, such as tetrahydrofuranyl, tetrahydrothienyl, dioxolanyl, dithiolanyl and oxathiolanyl, in particular tetrahydrofuranyl, tetrahydrothienyl or dioxolanyl, where these rings may be unsubstituted or may carry from one to three substituents selected from the group consisting of $C_1$–$C_4$-alkyl, $C_1$–$C_4$-alkoxy, $C_1$–$C_4$-alkylthio and $C_1$–$C_4$-haloalkyl;

a 5-membered heteroaromatic structure, such as pyrrolyl, pyrazolyl, imidazolyl, isoxazolyl, oxazolyl, isothiazolyl, thiazolyl, furanyl and thienyl, in particular isoxazolyl or furanyl, where the 5-membered heteroaromatic structure may be unsubstituted or may carry from one to three substituents selected from the group consisting of $C_1$–$C_4$-alkyl, $C_1$–$C_4$-alkoxy, $C_1$–$C_4$-alkylthio, $C_1$–$C_4$-haloalkyl, $C_1$–$C_4$-alkoxy-$C_1$–$C_4$-alkyl, such as methoxymethyl, 2-methoxyethyl, 2-methoxypropyl, 3-methoxypropyl, 2-methoxy-1-methylethyl, ethoxymethyl, 2-ethoxyethyl, 2-ethoxypropyl, 3-ethoxypropyl, 2-ethoxy-1-methylethyl and 1-ethoxy-1-methylethyl, preferably methoxyethyl and ethoxyethyl, $C_2$–$C_6$-alkenyl, such as ethenyl, and $C_3$–$C_6$-alkenyl, preferably 1-methylethen-1-yl, $C_2$–$C_6$-alkenyloxy, such as ethenyloxy, and $C_3$–$C_6$-alkenyloxy, in particular 1-methylethen-1-yloxy;

a 6-membered or 7-membered heterocyclic structure which a) may be saturated, eg. tetrahydropyran-3-yl, tetrahydropyran-4-yl, tetrahydrothiopyran-3-yl, tetrahydrothiopyran-4-yl and dioxepan-5-yl, or b) may be mono- or diunsaturated, eg. dihydropyran-3-yl, dihydropyran-4-yl, dihydrothiopyran-3-yl or dihydrothiopyran-4-yl, where the heterocyclic structures may be unsubstituted or may carry from one to three substituents selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl, very particularly preferably tetrahydropyran-3-yl, tetrahydropyran-4-yl and tetrahydrothiopyran-3-yl; phenyl or pyridyl, both of which may be unsubstituted or may carry from one to three substituents selected from the group consisting of $C_1$–$C_4$-alkyl, $C_1$–$C_4$-alkoxy, $C_1$–$C_4$-alkylthio, $C_1$–$C_4$-haloalkyl, $C_3$–$C_6$-alkenyloxy, preferably prop-2-en-1-yloxy or but-2-en-1-yloxy, $C_3$–$C_6$-alkynyloxy, such as 2-propynyloxy, 2-butynyloxy, 3-butynyloxy, 1-methyl-2-propynyloxy, 2-pentynyloxy, 3-pentynyloxy, 4-pentynyloxy, 1-methyl-3-butynyloxy, 2-methyl-3-butynyloxy, 1-methyl-2-butynyloxy, 1,1-dimethyl-2-propynyloxy, 1-ethyl-2-propynyloxy, 2-hexynyloxy, 3-hexynyloxy, 4-hexynyloxy, 5-hexynyloxy, 1-methyl-2-pentynyloxy, 1-methyl-3-pentynyloxy, 1-methyl-4-pentynyloxy, 2-methyl-3-pentynyloxy, 2-methyl-4-pentynyloxy, 3-methyl-4-pentynyloxy, 4-methyl-4-pentynyloxy, 1,1-dimethyl-2-butynyloxy, 1,1-dimethyl-3-butynyloxy, 1,2-dimethyl-3-butynyloxy, 2,2-dimethyl-3-butynyloxy, 1-ethyl-2-butynyloxy, 1-ethyl-3-butynyloxy, 2-ethyl-3-butynyloxy and 1-ethyl-1-methyl-2-propynyloxy, preferably 2-propynyloxy or 2-butynyloxy; one of the three substituents on the phenyl or pyridyl ring may furthermore be an amino group —$NR^aR^b$, where $R^a$ is hydrogen, $C_1$–$C_4$-alkyl, preferably methyl or ethyl, $C_3$–$C_6$-alkenyl, preferably prop-2-en-1-yl or but-2-en-1-yl, or $C_3$–$C_6$-alkynyl, preferably prop-2-yn-1-yl or but-2-yn-1-yl, and $R^b$ is hydrogen, $C_1$–$C_4$-alkyl, preferably methyl or ethyl, $C_3$–$C_6$-alkenyl, preferably prop-2-en-1-yl or but-2-en-1-yl, $C_3$–$C_6$-alkynyl, preferably prop-2-yn-1-yl or but-2-yn-1-yl, or $C_1$–$C_6$-acyl, such as acetyl, propionyl, n-butyryl, 2-methylpropionyl, n-pentanoyl, 2-methylbutyryl, 2-methylbutyryl, 2,2-dimethylpropionyl, n-hexanoyl, 2-methylpentanoyl, 3-methylpentanoyl, 4-methylpentanoyl, 2,2-dimethylbutyryl, 2,3-dimethylbutyryl, 3,3-dimethylbutyryl and 2-ethylbutyryl, preferably acetyl or propionyl, or benzoyl which may be unsubstituted or may in turn carry from one to three radicals selected from the group consisting of nitro, cyano, halogen, preferably fluorine, chlorine and bromine, $C_1$–$C_4$-alkyl, preferably methyl, $C_1$–$C_4$-alkoxy, preferably methoxy and ethoxy, $C_1$–$C_4$-alkylthio, preferably methylthio, and $C_1$–$C_4$-haloalkyl, preferably trifluoromethyl.

Suitable salts of the compounds of the formula I are agriculturally useful salts, for example alkali metal salts, in particular the sodium or potassium salt, alkaline earth metal salts, in particular the calcium, magnesium or barium salt, manganese, copper, zinc or iron salt and ammonium, phosphonium, sulfonium or sulfoxonium salts, for example ammonium salts, tetraalkylammonium salts, benzyltrialkylammonium salts, trialkylsulfonium salts or trialkylsulfoxonium salts.

Esters of $C_1$–$C_{10}$-carboxylic acids are understood as being in particular esters of $C_1$–$C_4$-alkanecarboxylic acids, such as methanecarboxylic acid (acetic acid), ethanecarboxylic acid (propionic acid), propanecarboxylic acid (butyric acid), 1-methylethanecarboxylic acid (isobutyric acid), butanecarboxylic acid, 1-methylpropanecarboxylic acid, 2-methylpropanecarboxylic acid, 1,1-dimethylethanecarboxylic acid, pentanecarboxylic acid, 1-methylbutanecarboxylic acid, 2-methylbutanecarboxylic acid, 3-methylbutanecarboxylic acid, 1,1-dimethylpropanecarboxylic acid, 1,2-dimethylpropanecarboxylic acid, 2,2-dimethylpropanecarboxylic acid, 1-ethylpropanecarboxylic acid, benzoic acid and halogen-substituted benzoic acids, hexanecarboxylic acid, 1-methylpentanecarboxylic acid, 2-methylpentanecarboxylic acid, 3-methylpentanecarboxylic acid, 4-methylpentanecarboxylic acid, 1,1-dimethylbutanecarboxylic acid, 1,2-dimethylbutanecarboxylic acid, 1,3-dimethylbutanecarboxylic acid, 2,2-dimethylbutanecarboxylic acid, 2,3-dimethylbutanecarboxylic acid, 3,3-dimethylbutanecarboxylic acid, 1-ethylbutanecarboxylic acid, 2-ethylbutanecarboxylic acid, 1,1,2-trimethylpropanecarboxylic acid, 1,2,2-trimethylpropanecarboxylic acid, 1-ethyl-1-methylpropanecarboxylic acid and 1-ethyl-2-methylpropanecarboxylic acid.

PREPARATION EXAMPLES

2-[1-[2-[4-(2,4-Dichlorophenoxy)phenoxy]propyloximino]-propyl]-3-hydroxy-5-(2H-tetrahydropyran-4-yl)-2-cyclo-hexen-1-one (4.04)

A mixture of 0.71 g (2.8 mmol) of 3-hydroxy-2-propionyl-5-(2H-tetrahydropyran-4-yl)-2-cyclohexen-1-one, 1.2 g (2.8 mmol) of 75% strength 0-[2-[4-(2,4-dichlorophenoxy)phenoxy]propylhydroxylamine and 100 ml of methanol was stirred for 24 hours at room temperature and then worked up in a known manner to give the product. Yield: 69%

$^1$H-NMR (200 MHz, in $CDCl_3$): δ [ppm]=1.15 (t, 3H), 1.20–1.45 (m, 6H), 1.65 (m, 2H), 1.90 (m, 1H), 2.25 (m, 2H), 2.60 (m, 2H); 2.85 (m, 2H), 3.35 (m, 2H), 4.00 (m, 2H), 4.25 (m, 2H), 4.60 (m, 1H), 6.80–7.55 (m, 7H).

INTERMEDIATE

0-[2-[4-(2,4-Dichlorophenoxy)phenoxy]propylhydroxylamine 7.5 g (0.043 mol) of diethyl azodicarboxylate were slowly added dropwise to a solution of 7.0 g (0.043 mol) of N-hydroxyphthalimide, 9.4 g (0.038 mol) of triphenylphosphine and 11.4 g (0.036 mol) of 2-[4-(2,4-dichlorophenoxy)phenoxy]-propan-1-ol (Z. Naturforsch. 37 B (1982), 912) in 250 ml of tetrahydrofuran. After a weakly exothermic reaction, working up was carried out after 15 hours in a known manner to give 16.3 g of the intermediate N-[2-[4-(2,4-dichlorophenoxy)phenoxy]propoxy]phthalimide.

200 ml of ethanolamine were then slowly added to this crude phthalimide product. After 3.5 hours at 60° C., the reaction mixture was poured into ice water and extracted with methylene chloride, and the combined organic phases were washed with water, dried over sodium sulfate and evaporated down under reduced pressure. Yield: 9.7 g (62% corrected) of 75% strength hydroxylamine (1.03).

$^1$H-NMR (200 MHz, in $CDCl_3$); δ [ppm]=1.30 (d, 3H), 3.80 (m, 2H), 4.65 (m, 1H), 5.55 (bs, 1H), 6.80–7.50 (m, 7H).

Novel hydroxylamines III are listed in Table 1 below. Tables 2 to 17 contain novel cyclohexenone oxime ethers I.

TABLE 1

$$H_2N-O-CH_2-\underset{CH_3}{\overset{*)}{CH}}-O-\phenyl-O-Z, \quad III$$

| No. | Z | *)Configuration | Phys. data ($^1$H-NMR [ppm], Rotational value $[\alpha]_D^{25}$) |
|---|---|---|---|
| 1.01 | 4-Chlorophenyl | (RS) | 4.20 (m, 2H), 4.60 (m, 1H), 6.80–7.35 (2m, 8H) |
| 1.02 | 4-Chlorophenyl | (R) | |
| 1.03 | 2,4-Dichlorophenyl | (RS) | 1.30 (d, 3H), 3.80 (m, 2H), |

TABLE 1-continued

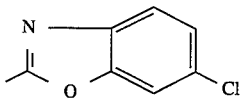

| No. | Z | *)Configuration | Phys. data (¹H-NMR [ppm], Rotational value $[\alpha]_D^{25}$) |
|---|---|---|---|
|  |  |  | 4.65 (m, 1H), 5.55 (bs, 1H), 6.80–7.50 (m, 7H) |
| 1.04 | 2,4-Dichlorophenyl | (R) | |
| 1.05 | 5-Trifluoromethyl-2-pyridyl | (RS) | |
| 1.06 | 5-Trifluoromethyl-2-pyridyl | (R) | |
| 1.07 | 3-Chloro-5-trifluoromethyl-2-pyridyl | (RS) | |
| 1.08 | 3-Chloro-5-trifluoromethyl-2-pyridyl | (R) | |
| 1.09 | 5-Chloro-3-fluoro-2-pyridyl | (RS) | |
| 1.10 | 5-Chloro-3-fluoro-2-pyridyl | (R) | |
| 1.11 | 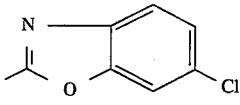 | (RS) | |
| 1.12 | 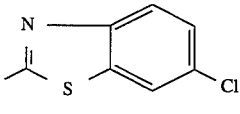 | (R) | |
| 1.13 | 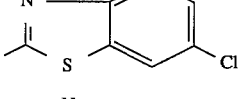 | (RS) | |
| 1.14 | 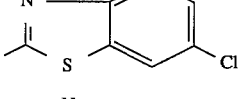 | (R) | |
| 1.15 | 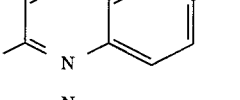 | (RS) | |
| 1.16 | 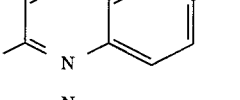 | (R) | |

TABLE 2

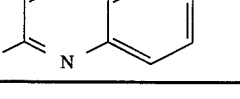

| No. | R¹ | R² | Phys. data (Rotational value $[\alpha]_D^{25}$; ¹H-NMR [ppm]) |
|---|---|---|---|
| 2.01 | Ethyl | (RS)-2H-Tetrahydropyran-3-yl | 3.80–4.00 (m, 2H), 4.20 (m, 2H), 4.60 (m, 1H), 6.80–7.35 (2m, 8H) |
| 2.02 | Ethyl | (R)-2H-Tetrahydropyran-3-yl | |
| 2.03 | Ethyl | (S)-2H-Tetrahydropyran-3-yl | |
| 2.04 | Ethyl | 2H-Tetrahydropyran-4-yl | 4.00 (m, 2H), 4.20 |

TABLE 2-continued

[Structure: Cyclohexenone with OH, R², C(R¹)=N-O-CH₂-*CH(CH₃)-O-phenyl-O-phenyl-Cl]   I

| No. | R¹ | R² | Phys. data (Rotational value $[\alpha]_D^{25}$; ¹H-NMR [ppm]) |
|---|---|---|---|
| | | | (m, 2H), 4.60 (m, 1H), 6.80–7.35 (2m, 8H) |
| 2.05 | Ethyl | (RS)-2H-Tetrahydrothiopyran-3-yl | 4.20 (m, 2H), 4.60 (m, 1H), 6.80–7.35 (2m, 8H) |
| 2.06 | Ethyl | (R)-2H-Tetrahydrothiopyran-3-yl | |
| 2.07 | Ethyl | (S)-2H-Tetrahydrothiopyran-3-yl | |
| 2.08 | Propyl | (RS)-2H-Tetrahydropyran-3-yl | 3.80–4.00 (m, 2H), 4.20 (m, 2H), 4.60 (m, 1H) 6.80–7.35 (2m, 8H) |
| 2.09 | Propyl | (R)-2H-Tetrahydropyran-3-yl | |
| 2.10 | Propyl | (S)-2H-Tetrahydropyran-3-yl | |
| 2.11 | Propyl | 2H-Tetrahydropyran-4-yl | 4.00 (m, 2H), 4.20 (m, 2H), 4.60 (m, 1H), 6.80–7.35 (2m, 8H) |
| 2.12 | Propyl | (RS)-2H-Tetrahydrothiopyran-3-yl | 4.20 (m, 2H), 4.60 (m, 1H) 6.80–7.35 (2m, 8H) |
| 2.13 | Propyl | (R)-2H-Tetrahydrothiopyran-3-yl | |
| 2.14 | Propyl | (S)-2H-Tetrahydrothiopyran-3-yl | |
| 2.15 | Ethyl | Phenyl | |
| 2.16 | Ethyl | 2,4,6-Trimethylphenyl | |
| 2.17 | Ethyl | 4-(Prop-2-ynyloxy)phenyl | |
| 2.18 | Propyl | 4-Fluoro-3-nitrophenyl | |
| 2.19 | Propyl | (RS)-2-(Ethylthio)prop-1-yl | |
| 2.20 | Ethyl | 1-Methylthiocycloprop-1-yl | |
| 2.21 | Ethyl | 1,3-Dimethylpyrazol-5-yl | |
| 2.22 | Propyl | 3-Isopropylisoxazol-5-yl | |
| 2.23 | Propyl | (RS)-Cyclohex-3-en-1-yl | |

(*)Racemate; RS configuration)

TABLE 3

[Structure: Cyclohexenone with OH, R², C(R¹)=N-O-CH₂-*CH(CH₃)-O-phenyl-O-phenyl-Cl]   I

| No. | R¹ | R² | Phys. data (Rotational value $[\alpha]_D^{25}$; ¹H-NMR [ppm]) |
|---|---|---|---|
| 3.01 | Ethyl | (RS)-2H-Tetrahydropyran-3-yl | |
| 3.02 | Ethyl | (R)-2H-Tetrahydropyran-3-yl | |
| 3.03 | Ethyl | (S)-2H-Tetrahydropyran-3-yl | |
| 3.04 | Ethyl | 2H-Tetrahydropyran-4-yl | |
| 3.05 | Ethyl | (RS)-2H-Tetrahydrothiopyran-3-yl | |
| 3.06 | Ethyl | (R)-2H-Tetrahydrothiopyran-3-yl | |
| 3.07 | Ethyl | (S)-2H-Tetrahydrothiopyran-3-yl | |
| 3.08 | Propyl | (RS)-2H-Tetrahydropyran-3-yl | |
| 3.09 | Propyl | (R)-2H-Tetrahydropyran-3-yl | |
| 3.10 | Propyl | (S)-2H-Tetrahydropyran-3-yl | |
| 3.11 | Propyl | 2H-Tetrahydropyran-4-yl | |
| 3.12 | Propyl | (RS)-2H-Tetrahydrothiopyran-3-yl | |
| 3.13 | Propyl | (R)-2H-Tetrahydrothiopyran-3-yl | |
| 3.14 | Propyl | (S)-2H-Tetrahydrothiopyran-3-yl | |

TABLE 3-continued

Structure I: cyclohexenone with OH, R², C(R¹)=N-O-CH₂-CH(CH₃)-O-[phenyl]-O-[phenyl]-Cl (*predominantly R configuration)

| No. | R¹ | R² | Phys. data (Rotational value $[\alpha]_D^{25}$; ¹H-NMR [ppm]) |
|---|---|---|---|
| 3.15 | Ethyl | Phenyl | |
| 3.16 | Ethyl | 2,4,6-Trimethylphenyl | |
| 3.17 | Ethyl | 4-(Prop-2-ynyloxy)phenyl | |
| 3.18 | Propyl | 4-Fluoro-3-nitrophenyl | |
| 3.19 | Propyl | (RS)-2-(Ethylthio)prop-1-yl | |
| 3.20 | Ethyl | 1-Methylthiocycloprop-1-yl | |
| 3.21 | Ethyl | 1,3-Dimethylpyrazol-5-yl | |
| 3.22 | Propyl | 3-Isopropylisoxazol-5-yl | |
| 3.23 | Propyl | (RS)-Cyclohex-3-en-1-yl | |

(*)predominantly R configuration

TABLE 4

Structure I: cyclohexenone with OH, R², C(R¹)=N-O-CH₂-CH(CH₃)-O-[phenyl]-O-[2,4-dichlorophenyl] (*predominantly R configuration)

| No. | R¹ | R² | Phys. data (Rotational value $[\alpha]_D^{25}$; ¹H-NMR [ppm]) |
|---|---|---|---|
| 4.01 | Ethyl | (RS)-2H-Tetrahydropyran-3-yl | 3.80–4.00 (m, 2H), 4.25 (m, 2H), 4.60 (m, 1H), 6.80–7.55 (m, 7H) |
| 4.02 | Ethyl | (R)-2H-Tetrahydropyran-3-yl | |
| 4.03 | Ethyl | (S)-2H-Tetrahydropyran-3-yl | |
| 4.04 | Ethyl | 2H-Tetrahydropyran-4-yl | 4.00 (m, 2H), 4.25 (m, 2H), 4.60 (m, 1H), 6.80–7.55 (m, 7H) |
| 4.05 | Ethyl | (RS)-2H-Tetrahydrothiopyran-3-yl | 4.25 (m, 2H), 4.60 (m, 1H), 6.80–7.55 (m, 7H) |
| 4.06 | Ethyl | (R)-2H-Tetrahydrothiopyran-3-yl | |
| 4.07 | Ethyl | (S)-2H-Tetrahydrothiopyran-3-yl | |
| 4.08 | Propyl | (RS)-2H-Tetrahydropyran-3-yl | 3.80–4.00 (m, 2H), 4.25 (m, 2H), 4.60 (m, 1H), 6.80–7.55 (m, 7H) |
| 4.09 | Propyl | (R)-2H-Tetrahydropyran-3-yl | |
| 4.10 | Propyl | (S)-2H-Tetrahydropyran-3-yl | |
| 4.11 | Propyl | 2H-Tetrahydropyran-4-yl | 4.00 (m, 2H), 4.25 (m, 2H), 4.60 (m, 1H), 6.80–7.55 (m, 7H) |
| 4.12 | Propyl | (RS)-2H-Tetrahydrothiopyran-3-yl | 4.25 (m, 2H), 4.60 (m, 1H), 6.80–7.55 (m, 7H) |
| 4.13 | Propyl | (R)-2H-Tetrahydrothiopyran-3-yl | |
| 4.14 | Propyl | (S)-2H-Tetrahydrothiopyran-3-yl | |
| 4.15 | Ethyl | Phenyl | |
| 4.16 | Ethyl | 2,4,6-Trimethylphenyl | |
| 4.17 | Ethyl | 4-(Prop-2-ynyloxy)phenyl | |
| 4.18 | Propyl | 4-Fluoro-3-nitrophenyl | |
| 4.19 | Propyl | (RS)-2-(Ethylthio)prop-1-yl | |

TABLE 4-continued

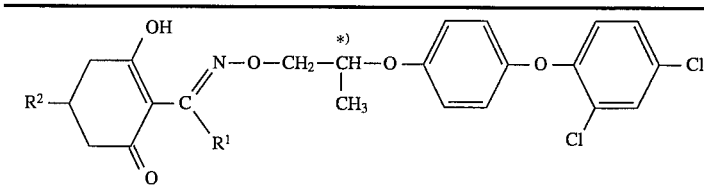

| No. | R¹ | R² | Phys. data (Rotational value $[\alpha]_D^{25}$; ¹H-NMR [ppm]) |
|---|---|---|---|
| 4.20 | Ethyl | 1-Methylthiocycloprop-1-yl | |
| 4.21 | Ethyl | 1,3-Dimethylpyrazol-5-yl | |
| 4.22 | Propyl | 3-Isopropylisoxazol-5-yl | |
| 4.23 | Propyl | (RS)-Cyclohex-3-en-1-yl | |

(*)Racemate; RS configuration)

TABLE 5

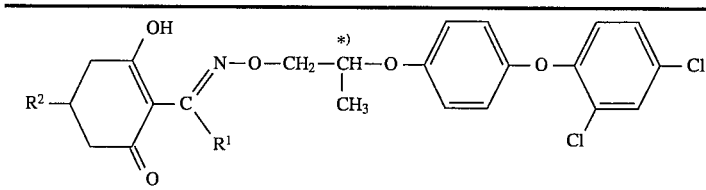

| No. | R¹ | R² | Phys. data (Rotational value $[\alpha]_D^{25}$; ¹H-NMR [ppm]) |
|---|---|---|---|
| 5.01 | Ethyl | (RS)-2H-Tetrahydropyran-3-yl | |
| 5.02 | Ethyl | (R)-2H-Tetrahydropyran-3-yl | |
| 5.03 | Ethyl | (S)-2H-Tetrahydropyran-3-yl | |
| 5.04 | Ethyl | 2H-Tetrahydropyran-4-yl | |
| 5.05 | Ethyl | (RS)-2H-Tetrahydrothiopyran-3-yl | |
| 5.06 | Ethyl | (R)-2H-Tetrahydrothiopyran-3-yl | |
| 5.07 | Ethyl | (S)-2H-Tetrahydrothiopyran-3-yl | |
| 5.08 | Propyl | (RS)-2H-Tetrahydropyran-3-yl | |
| 5.09 | Propyl | (R)-2H-Tetrahydropyran-3-yl | |
| 5.10 | Propyl | (S)-2H-Tetrahydropyran-3-yl | |
| 5.11 | Propyl | 2H-Tetrahydropyran-4-yl | |
| 5.12 | Propyl | (RS)-2H-Tetrahydrothiopyran-3-yl | |
| 5.13 | Propyl | (R)-2H-Tetrahydrothiopyran-3-yl | |
| 5.14 | Propyl | (S)-2H-Tetrahydrothiopyran-3-yl | |
| 5.15 | Ethyl | Phenyl | |
| 5.16 | Ethyl | 2,4,6-Trimethylphenyl | |
| 5.17 | Ethyl | 4-(Prop-2-ynyloxy)phenyl | |
| 5.18 | Propyl | 4-Fluoro-3-nitrophenyl | |
| 5.19 | Propyl | (RS)-2-(Ethylthio)prop-1-yl | |
| 5.20 | Ethyl | 1-Methylthiocycloprop-1-yl | |
| 5.21 | Ethyl | 1,3-Dimethylpyrazol-5-yl | |
| 5.22 | Propyl | 3-Isopropylisoxazol-5-yl | |
| 5.23 | Propyl | (RS)-Cyclohex-3-en-1-yl | |

(*)predominantly R configuration)

TABLE 6

$$\text{R}^2 \text{-cyclohexenone-OH-C(R}^1\text{)=N-O-CH}_2\text{-*CH(CH}_3\text{)-O-C}_6\text{H}_4\text{-O-pyridine-CF}_3 \quad \text{I}$$

| No. | R¹ | R² | Phys. data (Rotational value $[\alpha]_D^{25}$; ¹H-NMR [ppm]) |
|---|---|---|---|
| 6.01 | Ethyl | (RS)-2H-Tetrahydropyran-3-yl | |
| 6.02 | Ethyl | (R)-2H-Tetrahydropyran-3-yl | |
| 6.03 | Ethyl | (S)-2H-Tetrahydropyran-3-yl | |
| 6.04 | Ethyl | 2H-Tetrahydropyran-4-yl | |
| 6.05 | Ethyl | (RS)-2H-Tetrahydrothiopyran-3-yl | |
| 6.06 | Ethyl | (R)-2H-Tetrahydrothiopyran-3-yl | |
| 6.07 | Ethyl | (S)-2H-Tetrahydrothiopyran-3-yl | |
| 6.08 | Propyl | (RS)-2H-Tetrahydropyran-3-yl | |
| 6.09 | Propyl | (R)-2H-Tetrahydropyran-3-yl | |
| 6.10 | Propyl | (S)-2H-Tetrahydropyran-3-yl | |
| 6.11 | Propyl | 2H-Tetrahydropyran-4-yl | |
| 6.12 | Propyl | (RS)-2H-Tetrahydrothiopyran-3-yl | |
| 6.13 | Propyl | (R)-2H-Tetrahydrothiopyran-3-yl | |
| 6.14 | Propyl | (S)-2H-Tetrahydrothiopyran-3-yl | |
| 6.15 | Ethyl | Phenyl | |
| 6.16 | Ethyl | 2,4,6-Trimethylphenyl | |
| 6.17 | Ethyl | 4-(Prop-2-ynyloxy)phenyl | |
| 6.18 | Propyl | 4-Fluoro-3-nitrophenyl | |
| 6.19 | Propyl | (RS)-2-(Ethylthio)prop-1-yl | |
| 6.20 | Ethyl | 1-Methylthiocycloprop-1-yl | |
| 6.21 | Ethyl | 1,3-Dimethylpyrazol-5-yl | |
| 6.22 | Propyl | 3-Isopropylisoxazol-5-yl | |
| 6.23 | Propyl | (RS)-Cyclohex-3-en-1-yl | |

(*)Racemate; RS configuration)

TABLE 7

$$\text{R}^2 \text{-cyclohexenone-OH-C(R}^1\text{)=N-O-CH}_2\text{-*CH(CH}_3\text{)-O-C}_6\text{H}_4\text{-O-pyridine-CF}_3 \quad \text{I}$$

| No. | R¹ | R² | Phys. data (Rotational value $[\alpha]_D^{25}$; ¹H-NMR [ppm]) |
|---|---|---|---|
| 7.01 | Ethyl | (RS)-2H-Tetrahydropyran-3-yl | |
| 7.02 | Ethyl | (R)-2H-Tetrahydropyran-3-yl | |
| 7.03 | Ethyl | (S)-2H-Tetrahydropyran-3-yl | |
| 7.04 | Ethyl | 2H-Tetrahydropyran-4-yl | |
| 7.05 | Ethyl | (RS)-2H-Tetrahydrothiopyran-3-yl | |
| 7.06 | Ethyl | (R)-2H-Tetrahydrothiopyran-3-yl | |
| 7.07 | Ethyl | (S)-2H-Tetrahydrothiopyran-3-yl | |
| 7.08 | Propyl | (RS)-2H-Tetrahydropyran-3-yl | |
| 7.09 | Propyl | (R)-2H-Tetrahydropyran-3-yl | |
| 7.10 | Propyl | (S)-2H-Tetrahydropyran-3-yl | |
| 7.11 | Propyl | 2H-Tetrahydropyran-4-yl | |
| 7.12 | Propyl | (RS)-2H-Tetrahydrothiopyran-3-yl | |
| 7.13 | Propyl | (R)-2H-Tetrahydrothiopyran-3-yl | |
| 7.14 | Propyl | (S)-2H-Tetrahydrothiopy- |

TABLE 7-continued

[Structure: cyclohexanedione with OH, R², C=N-O-CH₂-CH(CH₃)-O-phenyl-O-pyridyl-CF₃, R¹; *) predominantly R]

| No. | R¹ | R² |
|---|---|---|
| | | ran-3-yl |
| 7.15 | Ethyl | Phenyl |
| 7.16 | Ethyl | 2,4,6-Trimethylphenyl |
| 7.17 | Ethyl | 4-(Prop-2-ynyloxy)phenyl |
| 7.18 | Propyl | 4-Fluoro-3-nitrophenyl |
| 7.19 | Propyl | (RS)-2-(Ethylthio)prop-1-yl |
| 7.20 | Ethyl | 1-Methylthiocycloprop-1-yl |
| 7.21 | Ethyl | 1,3-Dimethylpyrazol-5-yl |
| 7.22 | Propyl | 3-Isopropylisoxazol-5-yl |
| 7.23 | Propyl | (RS)-Cyclohex-3-en-1-yl |

Phys. data (Rotational value $[\alpha]_D^{25}$; $^1$H-NMR [ppm])

(*)predominantly R configuration)

TABLE 8

[Structure: cyclohexanedione with OH, R², C=N-O-CH₂-CH(CH₃)-O-phenyl-O-(3-chloro-5-trifluoromethyl-pyridyl), R¹; *) Racemate]

| No. | R¹ | R² |
|---|---|---|
| 8.01 | Ethyl | (RS)-2H-Tetrahydropyran-3-yl |
| 8.02 | Ethyl | (R)-2H-Tetrahydropyran-3-yl |
| 8.03 | Ethyl | (S)-2H-Tetrahydropyran-3-yl- |
| 8.04 | Ethyl | 2H-Tetrahydropyran-4-yl |
| 8.05 | Ethyl | (RS)-2H-Tetrahydrothiopyran-3-yl |
| 8.06 | Ethyl | (R)-2H-Tetrahydrothiopyran-3-yl |
| 8.07 | Ethyl | (S)-2H-Tetrahydrothiopyran-3-yl |
| 8.08 | Propyl | (RS)-2H-Tetrahydropyran-3-yl |
| 8.09 | Propyl | (R)-2H-Tetrahydropyran-3-yl |
| 8.10 | Propyl | (S)-2H-Tetrahydropyran-3-yl |
| 8.11 | Propyl | 2H-Tetrahydropyran-4-yl |
| 8.12 | Propyl | (RS)-2H-Tetrahydrothiopyran-3-yl |
| 8.13 | Propyl | (R)-2H-Tetrahydrothiopyran-3-yl |
| 8.14 | Propyl | (S)-2H-Tetrahydrothiopyran-3-yl |
| 8.15 | Ethyl | Phenyl |
| 8.16 | Ethyl | 2,4,6-Trimethylphenyl |
| 8.17 | Ethyl | 4-(Prop-2-ynyloxy)phenyl |
| 8.18 | Propyl | 4-Fluoro-3-nitrophenyl |
| 8.19 | Propyl | (RS)-2-(Ethylthio)prop-1-yl |
| 8.20 | Ethyl | 1-Methylthiocycloprop-1-yl |
| 8.21 | Ethyl | 1,3-Dimethylpyrazol-5-yl |
| 8.22 | Propyl | 3-Isopropylisoxazol-5-yl |
| 8.23 | Propyl | (RS)-Cyclohex-3-en-1-yl |

Phys. data (Rotational value $[\alpha]_D^{25}$; $^1$H-NMR [ppm])

(*)Racemate; RS configuration)

TABLE 9

$R^2$—[cyclohexenone with OH]—C(R¹)=N—O—CH₂—*CH(CH₃)—O—[phenyl]—O—[pyridine with Cl, CF₃]   I (*)predominantly R configuration

| No. | R¹ | R² | Phys. data (Rotational value $[\alpha]_D^{25}$; ¹H-NMR [ppm]) |
|---|---|---|---|
| 9.01 | Ethyl | (RS)-2H-Tetrahydropyran-3-yl | |
| 9.02 | Ethyl | (R)-2H-Tetrahydropyran-3-yl | |
| 9.03 | Ethyl | (S)-2H-Tetrahydropyran-n-3-yl | |
| 9.04 | Ethyl | 2H-Tetrahydropyran-4-yl | |
| 9.05 | Ethyl | (RS)-2H-Tetrahydrothiopyran-3-yl | |
| 9.06 | Ethyl | (R)-2H-Tetrahydrothiopyran-3-yl | |
| 9.07 | Ethyl | (S)-2H-Tetrahydrothiopyran-3-yl | |
| 9.08 | Propyl | (RS)-2H-Tetrahydropyran-3-yl | |
| 9.09 | Propyl | (R)-2H-Tetrahydropyran-3-yl | |
| 9.10 | Propyl | (S)-2H-Tetrahydropyran-3-yl | |
| 9.11 | Propyl | 2H-Tetrahydropyran-4-yl | |
| 9.12 | Propyl | (RS)-2H-Tetrahydrothiopyran-3-yl | |
| 9.13 | Propyl | (R)-2H-Tetrahydrothiopyran-3-yl | |
| 9.14 | Propyl | (S)-2H-Tetrahydrothiopyran-3-yl | |
| 9.15 | Ethyl | Phenyl | |
| 9.16 | Ethyl | 2,4,6-Trimethylphenyl | |
| 9.17 | Ethyl | 4-(Prop-2-ynyloxy)phenyl | |
| 9.18 | Propyl | 4-Fluoro-3-nitrophenyl | |
| 9.19 | Propyl | (RS)-2-(Ethylthio)prop-1-yl | |
| 9.20 | Ethyl | 1-Methylthiocycloprop-1-yl | |
| 9.21 | Ethyl | 1,3-Dimethylpyrazol-5-yl | |
| 9.22 | Propyl | 3-Isopropylisoxazol-5-yl | |
| 9.23 | Propyl | (RS)-Cyclohex-3-en-1-yl | |

TABLE 10

$R^2$—[cyclohexenone with OH]—C(R¹)=N—O—CH₂—*CH(CH₃)—O—[phenyl]—O—[pyridine with Cl]   I

| No. | R¹ | R² | Phys. data (Rotational value $[\alpha]_D^{25}$; ¹H-NMR [ppm]) |
|---|---|---|---|
| 10.01 | Ethyl | (RS)-2H-Tetrahydropyran-3-yl | |
| 10.02 | Ethyl | (R)-2H-Tetrahydropyran-3-yl | |
| 10.03 | Ethyl | (S)-2H-Tetrahydropyran-3-yl | |
| 10.04 | Ethyl | 2H-Tetrahydropyran-4-yl | |
| 10.05 | Ethyl | (RS)-2H-Tetrahydrothiopyran-3-yl | |
| 10.06 | Ethyl | (R)-2H-Tetrahydrothiopyran-3-yl | |
| 10.07 | Ethyl | (S)-2H-Tetrahydrothiopyran-3-yl | |
| 10.08 | Propyl | (RS)-2H-Tetrahydropyran-3-yl | |
| 10.09 | Propyl | (R)-2H-Tetrahydropyran-3-yl | |
| 10.10 | Propyl | (S)-2H-Tetrahydropyran-3-yl | |
| 10.11 | Propyl | 2H-Tetrahydropyran-4-yl | |
| 10.12 | Propyl | (RS)-2H-Tetrahydrothiopyran-3-yl | |
| 10.13 | Propyl | (R)-2H-Tetrahydrothiopyran-3-yl | |

TABLE 10-continued

Structure I: cyclohexanone with OH, R², and C(R¹)=N-O-CH₂-*CH(CH₃)-O-phenyl-O-pyridyl-Cl

| No. | R¹ | R² | Phys. data (Rotational value $[\alpha]_D^{25}$; ¹H-NMR [ppm] |
|---|---|---|---|
| 10.14 | Propyl | (S)-2H-Tetrahydrothiopyran-3-yl | |
| 10.15 | Ethyl | Phenyl | |
| 10.16 | Ethyl | 2,4,6-Trimethylphenyl | |
| 10.17 | Ethyl | 4-(Prop-2-ynyloxy)phenyl | |
| 10.18 | Propyl | 4-Fluoro-3-nitrophenyl | |
| 10.19 | Propyl | (RS)-2-(Ethylthio)prop-1-yl | |
| 10.20 | Ethyl | 1-Methylthiocycloprop-1-yl | |
| 10.21 | Ethyl | 1,3-Dimethylpyrazol-5-yl | |
| 10.22 | Propyl | 3-Isopropylisoxazol-5-yl | |
| 10.23 | Propyl | (RS)-Cyclohex-3-en-1-yl | |

(*)Racemate; RS configuration)

TABLE 11

Structure I: cyclohexanone with OH, R², and C(R¹)=N-O-CH₂-*CH(CH₃)-O-phenyl-O-(3-F, 5-Cl)pyridyl

| No. | R¹ | R² | Phys. data (Rotational value $[\alpha]_D^{25}$; ¹H-NMR [ppm] |
|---|---|---|---|
| 11.01 | Ethyl | (RS)-2H-Tetrahydropyran-3-yl | |
| 11.02 | Ethyl | (R)-2H-Tetrahydropyran-3-yl | |
| 11.03 | Ethyl | (S)-2H-Tetrahydropyran-3-yl | |
| 11.04 | Ethyl | 2H-Tetrahydropyran-4-yl | |
| 11.05 | Ethyl | (RS)-2H-Tetrahydrothiopyran-3-yl | |
| 11.06 | Ethyl | (R)-2H-Tetrahydrothiopyran-3-yl | |
| 11.07 | Ethyl | (S)-2H-Tetrahydrothiopyran-3-yl | |
| 11.08 | Propyl | (RS)-2H-Tetrahydropyran-3-yl | |
| 11.09 | Propyl | (R)-2H-Tetrahydropyran-3-yl | |
| 11.10 | Propyl | (S)-2H-Tetrahydropyran-3-yl | |
| 11.11 | Propyl | 2H-Tetrahydropyran-4-yl | |
| 11.12 | Propyl | (RS)-2H-Tetrahydrothiopyran-3-yl | |
| 11.13 | Propyl | (R)-2H-Tetrahydrothiopyran-3-yl | |
| 11.14 | Propyl | (S)-2H-Tetrahydrothiopyran-3-yl | |
| 11.15 | Ethyl | Phenyl | |
| 11.16 | Ethyl | 2,4,6-Trimethylphenyl | |
| 11.17 | Ethyl | 4-(Prop-2-ynyloxy)phenyl | |
| 11.18 | Propyl | 4-Fluoro-3-nitrophenyl | |
| 11.19 | Propyl | (RS)-2-(Ethylthio)prop-1-yl | |
| 11.20 | Ethyl | 1-Methylthiocycloprop-1-yl | |
| 11.22 | Ethyl | 1,3-Dimethylpyrazol-5-yl | |
| 11.22 | Propyl | 3-Isopropylisoxazol-5-yl | |
| 11.23 | Propyl | (RS)-Cyclohex-3-en-1-yl | |

(*)predominantly R configuration)

TABLE 12

| No. | R¹ | R² | Phys. data (Rotational value $[\alpha]_D^{25}$; ¹H-NMR [ppm] |
|---|---|---|---|
| 12.01 | Ethyl | (RS)-2H-Tetrahydropyran-3-yl | |
| 12.02 | Ethyl | (R)-2H-Tetrahydropyran-3-yl | |
| 12.03 | Ethyl | (S)-2H-Tetrahydropyran-3-yl | |
| 12.04 | Ethyl | 2H-Tetrahydropyran-4-yl | |
| 12.05 | Ethyl | (RS)-2H-Tetrahydrothiopyran-3-yl | |
| 12.06 | Ethyl | (R)-2H-Tetrahydrothiopyran-3-yl | |
| 12.07 | Ethyl | (S)-2H-Tetrahydrothiopyran-3-yl | |
| 12.08 | Propyl | (RS)-2H-Tetrahydropyran-3-yl | |
| 12.09 | Propyl | (R)-2H-Tetrahydropyran-3-yl | |
| 12.10 | Propyl | (S)-2H-Tetrahydropyran-3-yl | |
| 12.11 | Propyl | 2H-Tetrahydropyran-4-yl | |
| 12.12 | Propyl | (RS)-2H-Tetrahydrothiopyran-3-yl | |
| 12.13 | Propyl | (R)-2H-Tetrahydrothiopyran-3-yl | |
| 12.14 | Propyl | (S)-2H-Tetrahydrothiopyran-3-yl | |
| 12.15 | Ethyl | Phenyl | |
| 12.16 | Ethyl | 2,4,6-Trimethylphenyl | |
| 12.17 | Ethyl | 4-(Prop-2-ynyloxy)phenyl | |
| 12.18 | Propyl | 4-Fluoro-3-nitrophenyl | |
| 12.19 | Propyl | (RS)-2-(Ethylthio)prop-1-yl | |
| 12.20 | Ethyl | 1-Methylthiocycloprop-1-yl | |
| 12.21 | Ethyl | 1,3-Dimethylpyrazol-5-yl | |
| 12.22 | Propyl | 3-Isopropylisoxazol-5-yl | |
| 12.23 | Propyl | (RS)-Cyclohex-3-en-1-yl | |

(*)Racemate: RS configuration)

TABLE 13

| No. | R¹ | R² | Phys. data (Rotational value $[\alpha]_D^{25}$; ¹H-NMR [ppm] |
|---|---|---|---|
| 13.01 | Ethyl | (RS)-2H-Tetrahydropyran-3-yl | |
| 13.02 | Ethyl | (R)-2H-Tetrahydropyran-3-yl | |
| 13.03 | Ethyl | (S)-2H-Tetrahydropyran-3-yl | |
| 13.04 | Ethyl | 2H-Tetrahydropyran-4-yl | |
| 13.05 | Ethyl | (RS)-2H-Tetrahydrothiopyran-3-yl | |
| 13.06 | Ethyl | (R)-2H-Tetrahydrothiopyran-3-yl | |
| 13.07 | Ethyl | (S)-2H-Tetrahydrothiopyran-3-yl | |
| 13.08 | Propyl | (RS)-2H-Tetrahydropyran-3-yl | |
| 13.09 | Propyl | (R)-2H-Tetrahydropyran-3-yl | |
| 13.10 | Propyl | (S)-2H-Tetrahydropyran-3-yl | |
| 13.11 | Propyl | 2H-Tetrahydropyran-4-yl | |
| 13.12 | Propyl | (RS)-2H-Tetrahydrothiopyran-3-yl | |

TABLE 13-continued

Structure: R² on cyclohexenone with OH, connected via C(R¹)=N-O-CH₂-*CH(CH₃)-O-phenyl-O-C(=N-phenyl-Cl)-O (formula I)

| No. | R¹ | R² | Phys. data (Rotational value $[\alpha]_D^{25}$; ¹H-NMR [ppm] |
|---|---|---|---|
| 13.13 | Propyl | (R)-2H-Tetrahydrothiopyran-3-yl | |
| 13.14 | Propyl | (S)-2H-Tetrahydrothiopyran-3-yl | |
| 13.15 | Ethyl | Phenyl | |
| 13.16 | Ethyl | 2,4,6-Trimethylphenyl | |
| 13.17 | Ethyl | 4-(Prop-2-ynyloxy)phenyl | |
| 13.18 | Propyl | 4-Fluoro-3-nitrophenyl | |
| 13.19 | Propyl | (RS)-2-(Ethylthio)prop-1-yl | |
| 13.20 | Ethyl | 1-Methylthiocycloprop-1-yl | |
| 13.21 | Ethyl | 1,3-Dimethylpyrazol-5-yl | |
| 13.22 | Propyl | 3-Isopropylisoxazol-5-yl | |
| 13.23 | Propyl | (RS)-Cyclohex-3-en-1-yl | |

(*)predominantly R configuration)

TABLE 14

| No. | R¹ | R² | Phys. data (Rotational value $[\alpha]_D^{25}$; ¹H-NMR [ppm] |
|---|---|---|---|
| 14.01 | Ethyl | (RS)-2H-Tetrahydropyran-3-yl | |
| 14.02 | Ethyl | (R)-2H-Tetrahydropyran-3-yl | |
| 14.03 | Ethyl | (S)-2H-Tetrahydropyran-3-yl | |
| 14.04 | Ethyl | 2H-Tetrahydropyran-4-yl | |
| 14.05 | Ethyl | (RS)-2H-Tetrahydrothiopyran-3-yl | |
| 14.06 | Ethyl | (R)-2H-Tetrahydrothiopyran-3-yl | |
| 14.07 | Ethyl | (S)-2H-Tetrahydrothiopyran-3-yl | |
| 14.08 | Propyl | (RS)-2H-Tetrahydropyran-3-yl | |
| 14.09 | Propyl | (R)-2H-Tetrahydropyran-3-yl | |
| 14.10 | Propyl | (S)-2H-Tetrahydropyran-3-yl | |
| 14.11 | Propyl | 2H-Tetrahydropyran-4-yl | |
| 14.12 | Propyl | (RS)-2H-Tetrahydrothiopyran-3-yl | |
| 14.13 | Propyl | (R)-2H-Tetrahydrothiopyran-3-yl | |
| 14.14 | Propyl | (S)-2H-Tetrahydrothiopyran-3-yl | |
| 14.15 | Ethyl | Phenyl | |
| 14.16 | Ethyl | 2,4,6-Trimethylphenyl | |
| 14.17 | Ethyl | 4-(Prop-2-ynyloxy)pheny | |
| 14.18 | Propyl | 4-Fluoro-3-nitrophenyl | |
| 14.19 | Propyl | (RS)-2-(Ethylthio)prop-1-yl | |
| 14.20 | Ethyl | 1-Methylthiocycloprop-1-yl | |
| 14.21 | Ethyl | 1,3-Dimethylpyrazol-5-yl | |
| 14.22 | Propyl | 3-Isopropylisoxazol-5-yl | |
| 14.23 | Propyl | (RS)-Cyclohex-3-en-1-yl | |

(*)Racemate: RS configuration)

TABLE 15

[Structure I: cyclohexanedione oxime ether with CH₃-bearing stereocenter, phenoxy-benzoxazole bearing Cl substituent]

| No. | R¹ | R² | Phys. data (Rotational value [α]_D^25; ¹H-NMR [ppm] |
|---|---|---|---|
| 15.01 | Ethyl | (RS)-2H-Tetrahydropyran-3-yl | |
| 15.02 | Ethyl | (R)-2H-Tetrahydropyran-3-yl | |
| 15.03 | Ethyl | (S)-2H-Tetrahydropyran-3-yl | |
| 15.04 | Ethyl | 2H-Tetrahydropyran-4-yl | |
| 15.05 | Ethyl | (RS)-2H-Tetrahydrothiopyran-3-yl | |
| 15.06 | Ethyl | (R)-2H-Tetrahydrothiopyran-3-yl | |
| 15.07 | Ethyl | (S)-2H-Tetrahydrothiopyran-3-yl | |
| 15.08 | Propyl | (RS)-2H-Tetrahydropyran-3-yl | |
| 15.09 | Propyl | (R)-2H-Tetrahydropyran-3-yl | |
| 15.10 | Propyl | (S)-2H-Tetrahydropyran-3-yl | |
| 15.11 | Propyl | 2H-Tetrahydropyran-4-yl | |
| 15.12 | Propyl | (RS)-2H-Tetrahydrothiopyran-3-yl | |
| 15.13 | Propyl | (R)-2H-Tetrahydrothiopyran-3-yl | |
| 15.14 | Propyl | (S)-2H-Tetrahydrothiopyran-3-yl | |
| 15.15 | Ethyl | Phenyl | |
| 15.16 | Ethyl | 2,4,6-Trimethylphenyl | |
| 15.17 | Ethyl | 4-(Prop-2-ynyloxy)phenyl | |
| 15.18 | Propyl | 4-Fluoro-3-nitrophenyl | |
| 15.19 | Propyl | (RS)-2-(Ethylthio)prop-1-yl | |
| 15.20 | Ethyl | 1-Methylthiocycloprop-1-yl | |
| 15.21 | Ethyl | 1,3-Dimethylpyrazol-5-yl | |
| 15.22 | Propyl | 3-Isopropylisoxazol-5-yl | |
| 15.23 | Propyl | (RS)-Cyclohex-3-en-1-yl | |

(*)predominantly R configuration)

TABLE 16

[Structure I: cyclohexanedione oxime ether with CH₃-bearing stereocenter, phenoxy-quinoxaline bearing Cl substituent]

| No. | R¹ | R² | Phys. data (Rotational value [α]_D^25; ¹H-NMR [ppm] |
|---|---|---|---|
| 16.01 | Ethyl | (RS)-2H-Tetrahydropyran-3-yl | |
| 16.02 | Ethyl | (R)-2H-Tetrahydropyran-3-yl | |
| 16.03 | Ethyl | (S)-2H-Tetrahydropyran-3-yl | |
| 16.04 | Ethyl | 2H-Tetrahydropyran-4-yl | |
| 16.05 | Ethyl | (RS)-2H-Tetrahydrothiopyran-3-yl | |
| 16.06 | Ethyl | (R)-2H-Tetrahydrothiopyran-3-yl | |
| 16.07 | Ethyl | (S)-2H-Tetrahydrothiopyran-3-yl | |
| 16.08 | Propyl | (RS)-2H-Tetrahydropyran-3-yl | |
| 16.09 | Propyl | (R)-2H-Tetrahydropyran-3-yl | |
| 16.10 | Propyl | (S)-2H-Tetrahydropyran-3-yl | |
| 16.11 | Propyl | 2H-Tetrahydropyran-4-yl | |
| 16.12 | Propyl | (RS)-2H-Tetrahydrothiopyran-3-yl | |

TABLE 16-continued

Structure: R²-substituted cyclohexanone with OH, =N-O-CH₂-CH(*)(CH₃)-O-phenyl-O-C(=N)-quinoxaline-Cl, with R¹ substituent. Formula I.

| No. | R¹ | R² | Phys. data (Rotational value [α]$_D^{25}$; ¹H-NMR [ppm]) |
|---|---|---|---|
| 16.13 | Propyl | (R)-2H-Tetrahydrothiopyran-3-yl | |
| 16.14 | Propyl | (S)-2H-Tetrahydrothiopyran-3-yl | |
| 16.15 | Ethyl | Phenyl | |
| 16.16 | Ethyl | 2,4,6-Trimethylphenyl | |
| 16.17 | Ethyl | 4-(Prop-2-ynyloxy)phenyl | |
| 16.18 | Propyl | 4-Fluoro-3-nitrophenyl | |
| 16.19 | Propyl | (RS)-2-(Ethylthio)prop-1-yl | |
| 16.20 | Ethyl | 1-Methylthiocycloprop-1-yl | |
| 16.21 | Ethyl | 1,3-Dimethylpyrazol-5-yl | |
| 16.22 | Propyl | 3-Isopropylisoxazol-5-yl | |
| 16.23 | Propyl | (RS)-Cyclohex-3-en-1-yl | |

(*)Racemate; RS configuration

TABLE 17

Structure: same as above. Formula I.

| No. | R¹ | R² | Phys. data (Rotational value [α]$_D^{25}$; ¹H-NMR [ppm]) |
|---|---|---|---|
| 17.01 | Ethyl | (RS)-2H-Tetrahydropyran-3-yl | |
| 17.02 | Ethyl | (R)-2H-Tetrahydropyran-3-yl | |
| 17.03 | Ethyl | (S)-2H-Tetrahydropyran-3-yl | |
| 17.04 | Ethyl | 2H-Tetrahydropyran-4-yl | |
| 17.05 | Ethyl | (RS)-2H-Tetrahydrothiopyran-3-yl | |
| 17.06 | Ethyl | (R)-2H-Tetrahydrothiopyran-3-yl | |
| 17.07 | Ethyl | (S)-2H-Tetrahydrothiopyran-3-yl | |
| 17.08 | Propyl | (RS)-2H-Tetrahydropyran-3-yl | |
| 17.09 | Propyl | (R)-2H-Tetrahydropyran-3-yl | |
| 17.10 | Propyl | (S)-2H-Tetrahydropyran-3-yl | |
| 17.11 | Propyl | 2H-Tetrahydropyran-4-yl | |
| 17.12 | Propyl | (RS)-2H-Tetrahydrothiopyran-3-yl | |
| 17.13 | Propyl | (R)-2H-Tetrahydrothiopyran-3-yl | |
| 17.14 | Propyl | (S)-2H-Tetrahydrothiopyran-3-yl | |
| 17.15 | Ethyl | Phenyl | |
| 17.16 | Ethyl | 2,4,6-Trimethylphenyl | |
| 17.17 | Ethyl | 4-(Prop-2-ynyloxy)phenyl | |
| 17.18 | Propyl | 4-Fluoro-3-nitrophenyl | |
| 17.19 | Propyl | (RS)-2-(Ethylthio)prop-1-yl | |
| 17.20 | Ethyl | 1-Methylthiocycloprop-1-yl | |
| 17.21 | Ethyl | 1,3-Dimethylpyrazol-5-yl | |
| 17.22 | Propyl | 3-Isopropylisoxazol-5-yl | |
| 17.23 | Propyl | (RS)-Cyclohex-3-en-1-yl | |

(*)predominantly R configuration

The optically active cyclohexenone oxime ethers I are suitable, both as isomer mixtures and in the form of the pure isomers, as herbicides especially for combating plants from the Gramineae species. They are generally well tolerated and are thus selective in broadleaved crops and in monocotyledons not belonging to the Gramineae. Some of the cyclohexenone oxime ethers I according to the invention are also suitable for selectively combating unwanted grasses in Gramineae.

The optically active cyclohexenone oxime ethers I, or herbicidal agents containing them, may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they should ensure as fine a distribution of the active ingredients according to the invention as possible.

The compositions I are generally suitable for the preparation of solutions, emulsions, pastes and oil dispersions to be sprayed direct. Examples of suitable inert additives are mineral oil fractions of medium to high boiling point, such as kerosene or diesel oil, further coal-tar oils, and oils of vegetable or animal origin, aliphatic, cyclic and aromatic hydrocarbons such as toluene, xylene, paraffin, tetrahydronaphthalene, alkylated naphthalenes and their derivatives, methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc.

Aqueous formulations may be prepared from emulsion concentrates, pastes, oil dispersions, wettable powders or water-dispersible granules by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxylpropylene, lauryl alcohol polyglycol ether acetal, sorbitol esters, ligninsulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acids, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

The formulations contain from 0.01 to 95, and preferably 0.5 to 90%, by weight of active ingredient. The active ingredients are used in a purity of 90 to 100, and preferably 95 to 100%, (according to the NMR spectrum).

Examples of formulations are as follows:

I. A solution of 90 parts by weight of compound no. 2.01 and 10 parts by weight of N-methyl-α-pyrrolidone, which is suitable for application in the form of very fine drops.

II. A mixture of 20 parts by weight of compound no. 2.03, 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By finely dispersing the mixture in 100,000 parts by weight of water, an aqueous dispersion containing 0.02 wt % of the active ingredient is obtained.

III. An aqueous dispersion of 20 parts by weight of compound no. 2.05, 40 parts by weight of cyclohexanone, 30 parts by weight of isobutanol, 20 parts by weight of the adduct of 40 moles of ethylene oxide and 1 mole of castor oil. A mixture of this dispersion with 100,000 parts by weight of water contains 0.02 wt % of the active ingredient.

IV. An aqueous dispersion of 20 parts by weight of compound no. 2.07, 25 parts by weight of cyclohexanone, 65 parts by weight of a mineral oil fraction having a boiling point of from 210° to 280° C., and 10 parts by weight of the adduct of 40 moles of ethylene oxide and 1 mole of castor oil. The mixture of this dispersion with 100,000 parts by weight of water contains 0.02 wt % of the active ingredient.

V. A hammer-milled mixture of 80 parts by weight of compound no. 2.09, 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel. By finely dispersing the mixture in 20,000 parts by weight of water, a spray liquor containing 0.1 wt % of the active ingredient is obtained.

VI. An intimate mixture of 3 parts by weight of compound no. 2.11 and 97 parts by weight of particulate kaolin. The dust contains 3 wt % of the active ingredient.

VII. An intimate mixture of 30 parts by weight of compound no. 2.13, 92 parts by weight of powdered silica gel and 8 parts by weight of paraffin oil sprayed onto the surface of this silica gel. This formulation of the active ingredient exhibits good adherence.

VIII. A stable aqueous dispersion of 40 parts by weight of compound no. 2.15, 10 parts of the sodium salt of a phenolsulfonic acid-urea-formaldehyde condensate, 2 parts of silica gel and 48 parts of water, which dispersion can be further diluted.

IX. A stable oily dispersion of 20 parts by weight of compound no. 3.01, 2 parts by weight of the calcium salt of dodecylbenzenesulfonic acid, 8 parts by weight of a fatty alcohol polyglycol ether, 20 parts by weight of the sodium salt of a phenolsulfonic acid-urea-formaldehyde condensate and 68 parts by weight of a paraffinic mineral oil.

X. A hammer-milled mixture of 10 parts by weight of compound no. 4.03, 4 parts by weight of the sodium salt of diisobutylnaphthalene-α-sulfonic acid, 20 parts by weight of the sodium salt of a lignin-sulfonic acid obtained from a sulfite waste liquor, and 38 parts by weight of silica gel and 38 parts by weight of kaolin. By finely dispersing the mixture in 10,000 parts by weight of water, a spray liquor containing 0.1 wt % of the active ingredient is obtained.

The active ingredients or the herbicidal agents containing them may be applied pre- or postemergence. If certain crop plants tolerate the active ingredients less well, application techniques may be used in which the herbicidal agents are sprayed from suitable equipment in such a manner that the leaves of sensitive crop plants are if possible not touched, and the agents reach the uncovered soil or the leaves of unwanted plants growing beneath the crop plants (post-directed, lay-by treatment).

The application rates depend on the objective to be achieved, the time of the year, the plants to be combated and their growth stage, and are from 0.001 to 3, preferably 0.01 to 1, kg of active ingredient per hectare.

In view of the numerous application methods possible, the cyclohexenone oxime ethers I or the agents containing them may also be used in a further number of crops for eliminating unwanted plants. Those which follow are given by way of example:

| | |
|---|---|
| *Allium cepa* | onions |
| *Ananas comosus* | pineapples |
| *Arachis hypogaea* | peanuts (groundnuts) |
| *Asparagus officinalis* | asparagus |
| *Beta vuigaris* spp. *altissima* | sugarbeets |
| *Beta vuigaris* spp. *rapa* | fodder beets |
| *Brassica napus* var. *napus* | rapeseed |
| *Brassica napus* var. *napobrassica* | swedes |
| *Brassica rapa* var. *silvestris* | |
| *Camellia sinensis* | tea plants |
| *Carthamus tinctorius* | safflower |
| *Carya illinoinensis* | pecan trees |
| *Citrus limon* | lemons |
| *citrus sinensis* | orange trees |
| *Coffea arabica* (*Coffea canephora, Coffea liberica*) | coffee plants |
| *Cucumis sativus* | cucumbers |
| *Cynodon dactylon* | Bermudagrass |
| *Daucus carota* | carrots |
| *Elais guineensis* | oil palm |
| *Fragaria vesca* | strawberries |
| *Glycine max* | soybeans |
| *Gossypium hirsutum* (*Gossypium arboreum, Gossypium herbaceum, Gossypium vitifolium*) | cotton |
| *Helianthus annuus* | sunflowers |
| *Hevea brasiliensis* | rubber plants |
| *Hordeum vulgare* | barley |
| *Humulus lupulus* | hops |
| *Ipomoea batatas* | sweet potatoes |
| *Juglans regia* | walnut trees |
| *Lens culinaris* | lentils |
| *Linum usitatissimum* | flax |
| *Lycopersicon lycopersicum* | tomatoes |
| *Malus* spp. | apple trees |
| *Manihot esculenta* | cassava |
| *Medicago sativa* | alfalfa (lucerne) |
| *Musa* spp. | banana plants |
| *Nicotiana tabacum* (*N. rustics*) | tobacco |
| *Olea europaea* | olive trees |
| *Oryza sativa* | rice |
| *Phaseolus lunatus* | limabeans |
| *Phaseolus vulgaris* | snapbeans, green beans, dry beans |
| *Picea abies* | Norway spruce |
| *Pinus* spp. | pine trees |

-continued

| | |
|---|---|
| *Pisum sativum* | English peas |
| *Prunus avium* | cherry trees |
| *Prunus persica* | peach trees |
| *Pyrus communis* | pear trees |
| *Ribes sylvestre* | redcurrants |
| *Ricinus communis* | castor-oil plants |
| *Saccharum officinarum* | sugar cane |
| *Secale cereale* | rye |
| *Solanum tuberosum* | Irish potatoes |
| *Sorghum bicolor* (s. *vulgare*) | sorghum |
| *Theobroma cacao* | cacao plants |
| *Trifolium pratense* | red clover |
| *Triticum aestivum* | wheat |
| *Triticum durum* | wheat |
| *Vicia faba* | tick beans |
| *Vitis vinitera* | grapes |
| *Zea mays* | Indian corn, sweet corn, maize |

To increase the spectrum of action and to achieve synergistic effects, the cyclohexenone oxime ethers I may be mixed and applied together with numerous representatives of other herbicidal or growth-regulating active ingredient groups. Examples of suitable components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives bearing in the 2-position for example a carboxy or carbimino group, quinolinecarboxylic acids, imidazolinones, sulfonamides, sulfonylureas, (hetero)-aryloxyphenoxypropionic acids and salts, esters, amides thereof, etc.

It may also be useful to apply the compounds I, either alone or in combination with other herbicides, in admixture with other crop protection agents, e.g., agents for combating pests or phytopathogenic fungi or bacteria. Further interest attaches to the miscibility with solutions of mineral salts used to remedy nutritional or trace element deficiencies. Non-phytotoxic oils and oil concentrates may also be added.

USE EXAMPLES

The herbicidal action of the unsaturated cyclohexenone oxime ethers of the formula I is demonstrated in greenhouse experiments:

The vessels employed were plastic flowerpots filled with a sandy loam containing about 3.0% humus. The seeds of the test plants were sown separately, according to species.

For the preemergence treatment, the active ingredients, emulsified or suspended in water were applied immediately after the seeds had been sown, and sprayed through finely distributing nozzles. The vessels were lightly sprinkler-irrigated to induce germination and growth. Transparent plastic covers were then placed on the vessels until the plants had taken root. The cover ensured uniform germination of the plants, insofar as this was not impaired by the active ingredients.

For the postemergence treatment, plants were used which had been sown in the pots and grown there, or they were grown separately as seedlings and transplanted to the pots a few days before treatment. The plants were grown, depending on growth form, to a height of 3 to 15 cm before being treated with the compounds, suspended or emulsified in water. The application rate for postemergence treatment was 0.25 kg/ha.

The pots were set up, at temperatures specific to their species, of 20° to 35° C., or 10° to 25° C. The experiments were run for from 2 to 4 weeks. During this period the plants were tended and their reactions to the various treatments assessed.

The assessment scale was 0 to 100,100 denoting non-emergence or complete destruction of at least the visible plant parts, and 0 denoting no damage or normal growth.

We claim:

1. Mixtures of optically active cyclohexenone oxime ethers, having R- and S-configuration in the oxime ether moiety and containing at least 50 mol % of the R-configuration, of the formula I

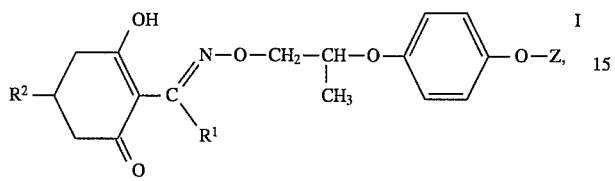

where:

$R^1$ is $C_1$–$C_6$-alkyl

Z is one of the following groups:

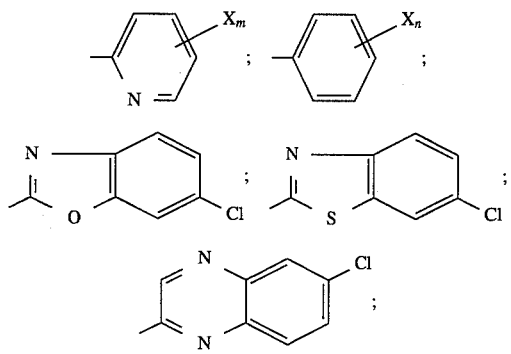

X is halogen or $C_1$–$C_4$-haloalkyl;

m is from 0 to 3, or from 1 to 4 where all X's are halogen;

n is from 0 to 3, or from 1 to 5 where all X's are halogen;

$R^2$ is $C_1$–$C_4$-alkoxy-$C_1$–$C_6$-alkyl or $C_1$–$C_4$-alkylthio-$C_1$–$C_6$-alkyl; $C_3$–$C_7$-cycloalkyl or $C_5$–$C_7$-cycloalkenyl, where these groups are unsubstituted or bear from one to three substituents selected from the group consisting of $C_1$–$C_4$-alkyl, $C_1$–$C_4$-alkoxy, $C_1$–$C_4$-alkylthio, $C_1$–$C_4$-haloalkyl, hydroxyl and halogen;

the 5-membered heterocyclic structure tetrahydrofuranyl tetrahydrothienyl or dioxolanyl, which heterocyclic structure is unsubstituted or bears from one to three substituents selected from the group consisting of $C_1$–$C_4$-alkyl, $C_1$–$C_4$-alkoxy, $C_1$–$C_4$-alkylthio and $C_1$–$C_4$-haloalkyl; a 6- or 7-membered saturated or mono- or diunsaturated heterocyclic structure which in addition to the carbon atoms of the ring has one or two oxygen or sulfur atoms or one oxygen and one sulfur atom as heteroatoms and which is unsubstituted or bears from one to three substituents selected from the group consisting of hydroxyl, halogen, $C_1$–$C_4$-alkyl, $C_1$–$C_4$-alkoxy, $C_1$–$C_4$-alkylthio and $C_1$–$C_4$-haloalkyl; a 5-membered heteroaromatic structure selected from the group consisting of isoxazolyl and furanyl, which heteroaromatic structure is unsubstituted or bears from one to three substituents selected from the group consisting of halogen, cyano, $C_1$–$C_4$-alkyl, $C_1$–$C_4$-alkoxy, $C_1$–$C_4$-alkylthio, $C_1$–$C_4$-haloalkyl, $C_2$–$C_6$-alkenyl, $C_2$–$C_6$-alkenyloxy and $C_1$–$C_4$-alkoxy-$C_1$–$C_4$-alkyl;

phenyl or pyridyl, where these aromatic structures are unsubstituted or bear from one to three substituents selected from the group consisting of nitro, $C_1$–$C_4$-alkyl, and $C_3$–$C_6$-alkynyloxy or the agriculturally useful salts and esters of the compounds I with $C_1$–$C_{10}$-carboxylic acids.

2. Optically active cyclohexenone oxime ethers I as set forth in claim 1 having from 90 to 100 mol % of the R-configuration in the oxime ether moiety.

3. Mixtures of optically active cyclohexenone oxime ethers as defined in claim 1, wherein in formula I, Z is phenyl, X is halogen and n is 0 to 3.

4. Mixtures of optically active cyclohexenone oxime ethers of the formula I, as defined in claim 1, wherein $R^1$ is ethyl, $R^2$ is 2H-tetrahydropyran-4-yl and Z is 2,4-dichlorophenyl.

5. A herbicidal composition containing inert additives and a herbicidally effective amount of a mixture of optically active cyclohexenone oxime ethers of the formula I as set forth in claim 1.

6. A method of combating the growth of unwanted plants, wherein a herbicidally effective amount of a mixture of optically active cyclohexenone oxime ethers I as set forth in claim 1 is allowed to act on the plants, their habitat or their seed.

* * * * *